(12) United States Patent
Fujii

(10) Patent No.: US 10,213,092 B2
(45) Date of Patent: Feb. 26, 2019

(54) SHEATH ASSEMBLY, MANIPULATOR, AND MANIPULATOR SYSTEM

(71) Applicant: OLYMPUS CORPORATION, Tokyo (JP)

(72) Inventor: Yuta Fujii, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/604,922

(22) Filed: May 25, 2017

(65) Prior Publication Data

US 2017/0258300 A1 Sep. 14, 2017

Related U.S. Application Data

(63) Continuation of application No. PCT/JP2016/063348, filed on Apr. 28, 2016.

(30) Foreign Application Priority Data

May 28, 2015 (JP) .................................. 2015-108235

(51) Int. Cl.
*A61B 1/00* (2006.01)
*A61B 1/005* (2006.01)
(Continued)

(52) U.S. Cl.
CPC ........ *A61B 1/00135* (2013.01); *A61B 1/0052* (2013.01); *A61B 1/00133* (2013.01);
(Continued)

(58) Field of Classification Search
CPC ..... A61B 1/00135; A61B 1/04; A61B 1/0052; A61B 1/00133; A61B 1/018; A61B 1/0057; A61B 1/0056
See application file for complete search history.

(56) References Cited

U.S. PATENT DOCUMENTS 4,745,908 A 5/1988 Wardle
7,744,608 B2 6/2010 Lee et al.
(Continued)

FOREIGN PATENT DOCUMENTS

CN 1547448 A 11/2004
CN 101061943 A 10/2007
(Continued)

OTHER PUBLICATIONS

Low-Inductance DIY Braided Hi-Fi Speaker Cables, McCall, 5 pages.*
(Continued)

*Primary Examiner* — Timothy J Neal
(74) *Attorney, Agent, or Firm* — Scully, Scott, Murphy & Presser, P.C.

(57) ABSTRACT

A sheath assembly 6 includes at least three flexible, tubular members 6a, 6b and 6c through which linear members can be inserted, a first holder 61 configured to hold one end side of the tubular members 6a, 6b and 6c, and a second holder 62 configured to hold the other end side of the tubular members 6a, 6b and 6c, wherein the first holder 61 and the second holder 62 hold the at least three tubular members 6a, 6b and 6c such that sections of the tubular members 6a, 6b and 6c orthogonal to an axial direction thereof are linearly aligned.

13 Claims, 15 Drawing Sheets

(51) Int. Cl.
    *A61B 1/018*     (2006.01)
    *A61B 1/04*     (2006.01)
    *A61B 34/37*     (2016.01)

(52) U.S. Cl.
    CPC ............... *A61B 1/018* (2013.01); *A61B 1/04* (2013.01); *A61B 34/37* (2016.02)

(56) References Cited

U.S. PATENT DOCUMENTS

| | | |
|---|---|---|
| 2001/0029317 A1 | 10/2001 | Hayakawa |
| 2011/0237891 A1 | 9/2011 | Sato et al. |
| 2015/0119638 A1 | 4/2015 | Yu et al. |

FOREIGN PATENT DOCUMENTS

| | | |
|---|---|---|
| EP | 0 029 344 A2 | 5/1981 |
| JP | 2009-066299 A | 4/2009 |
| JP | 2014-057849 A | 4/2014 |
| WO | WO 2011/052372 A1 | 5/2011 |

OTHER PUBLICATIONS

PTFE Cables & Wires—Mult Core Cables Manufacturer from Mumbai, Bhuwal Cables Limited, 35 pages.*
International Search Report dated Jul. 26, 2016 issued in PCT/JP2016/063348.
Extended Supplementary European Search Report dated Jan. 8, 2019 in European Patent Application No. 16 79 9757.6.

* cited by examiner

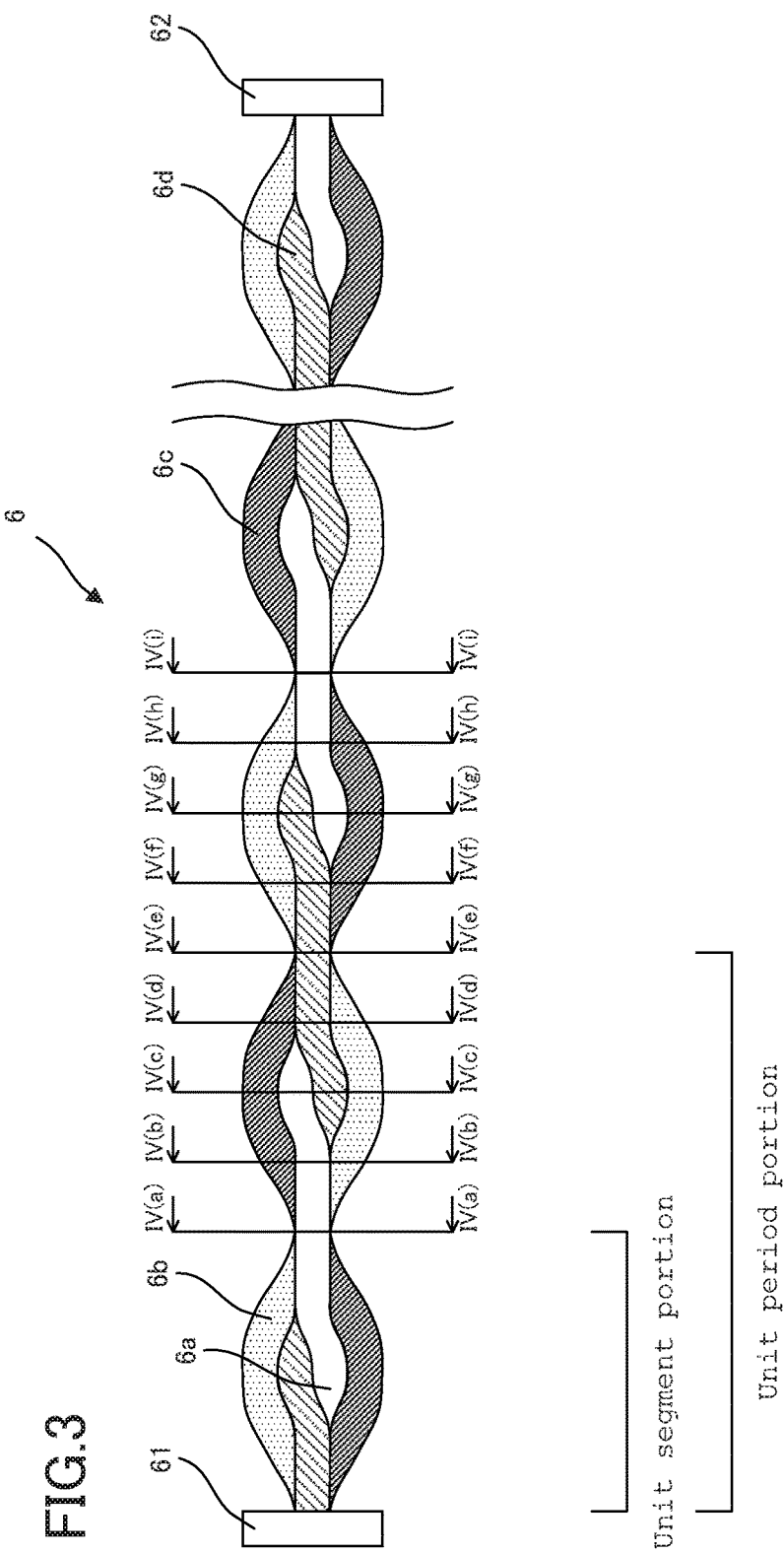

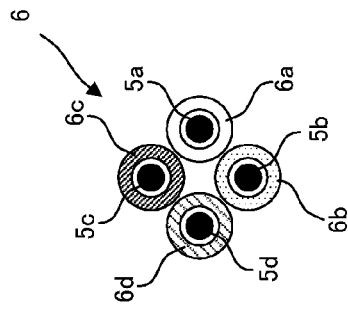
FIG.4D
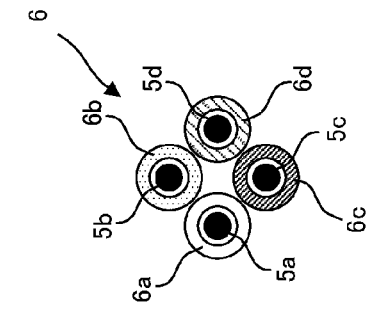
FIG.4H
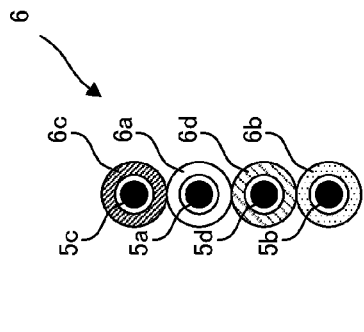
FIG.4C
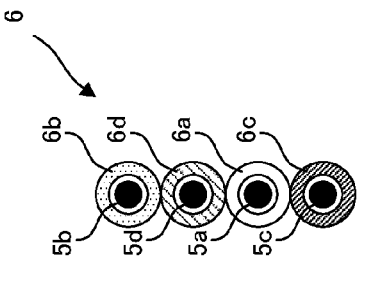
FIG.4G
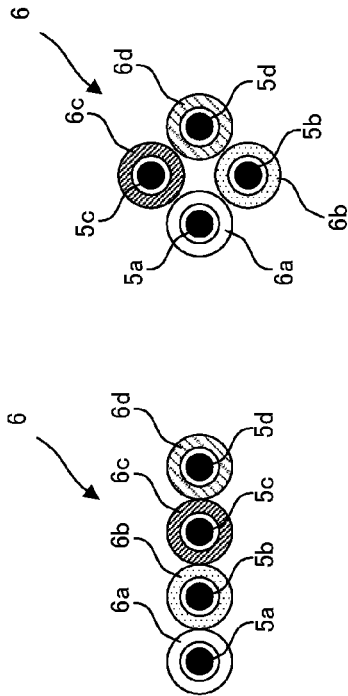
FIG.4B
FIG.4A
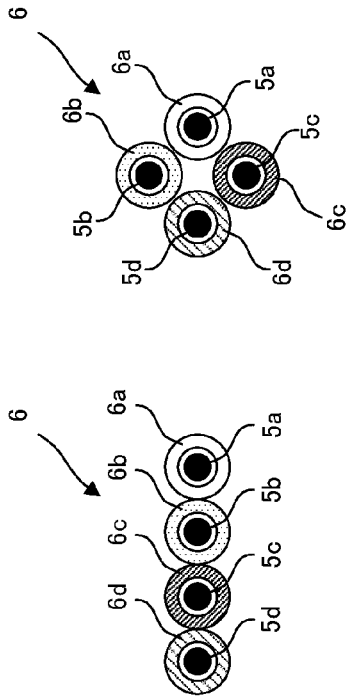
FIG.4F
FIG.4E

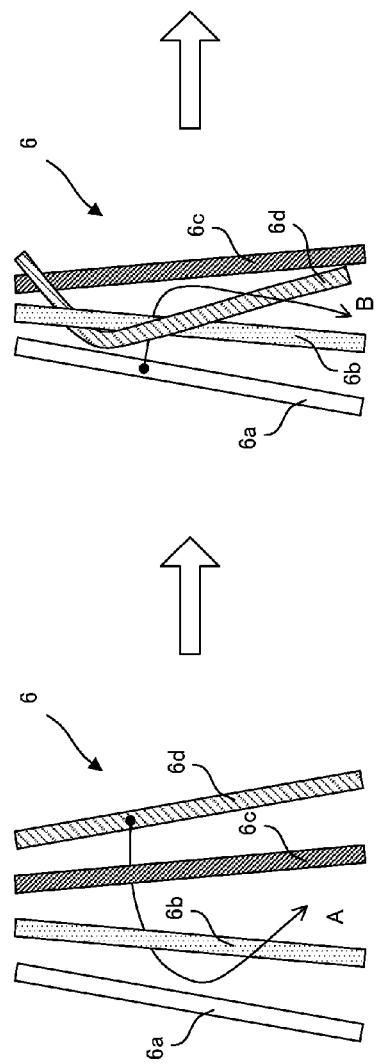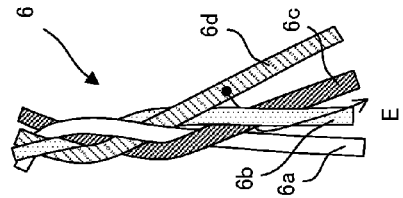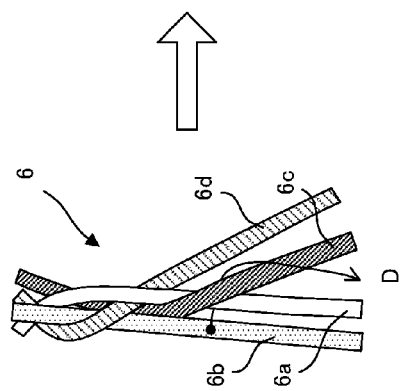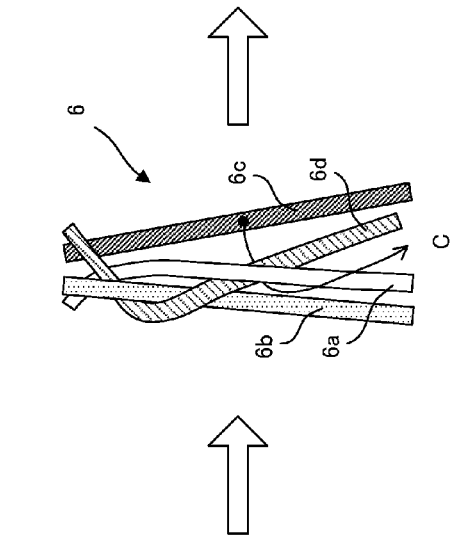

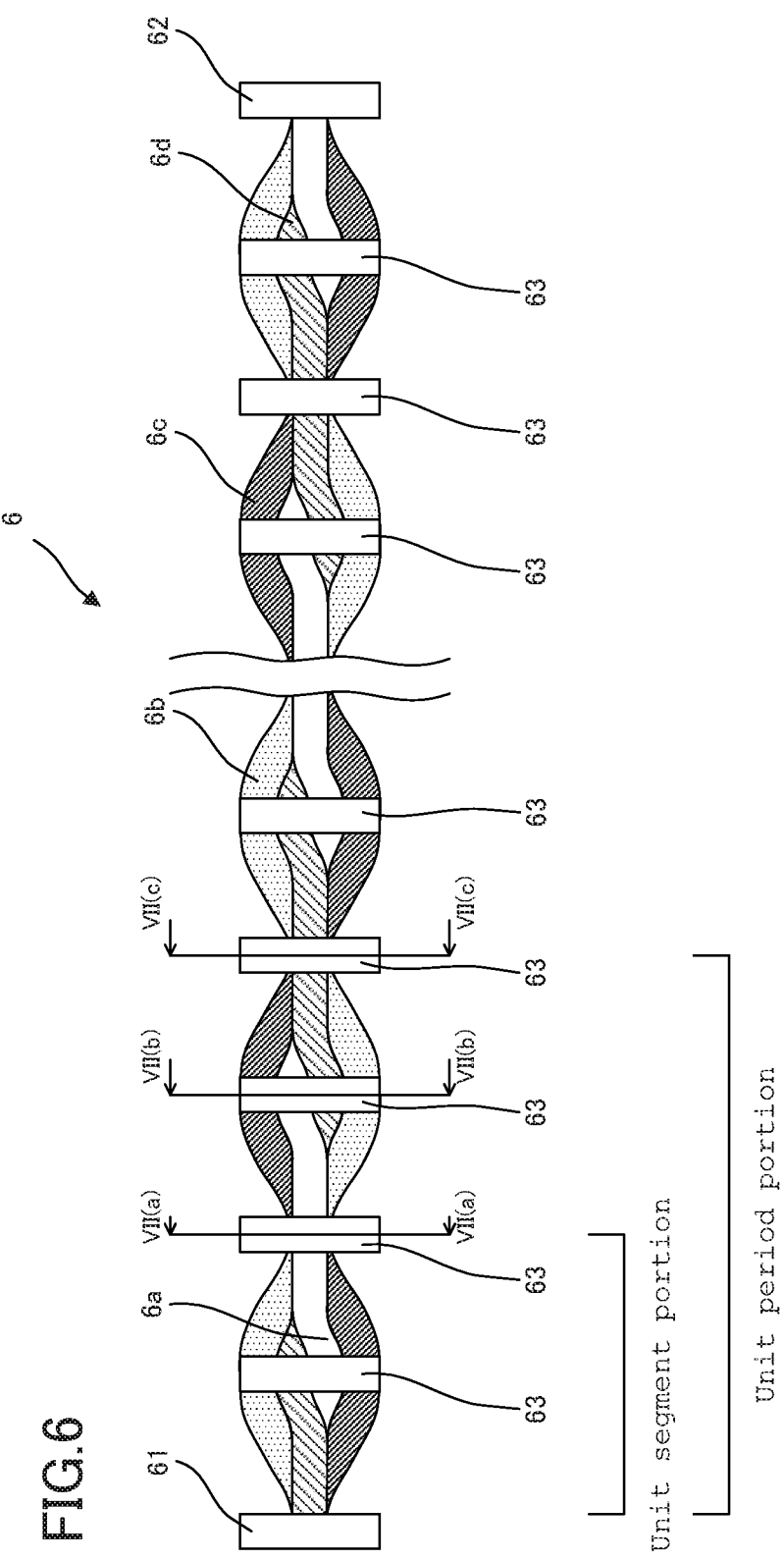

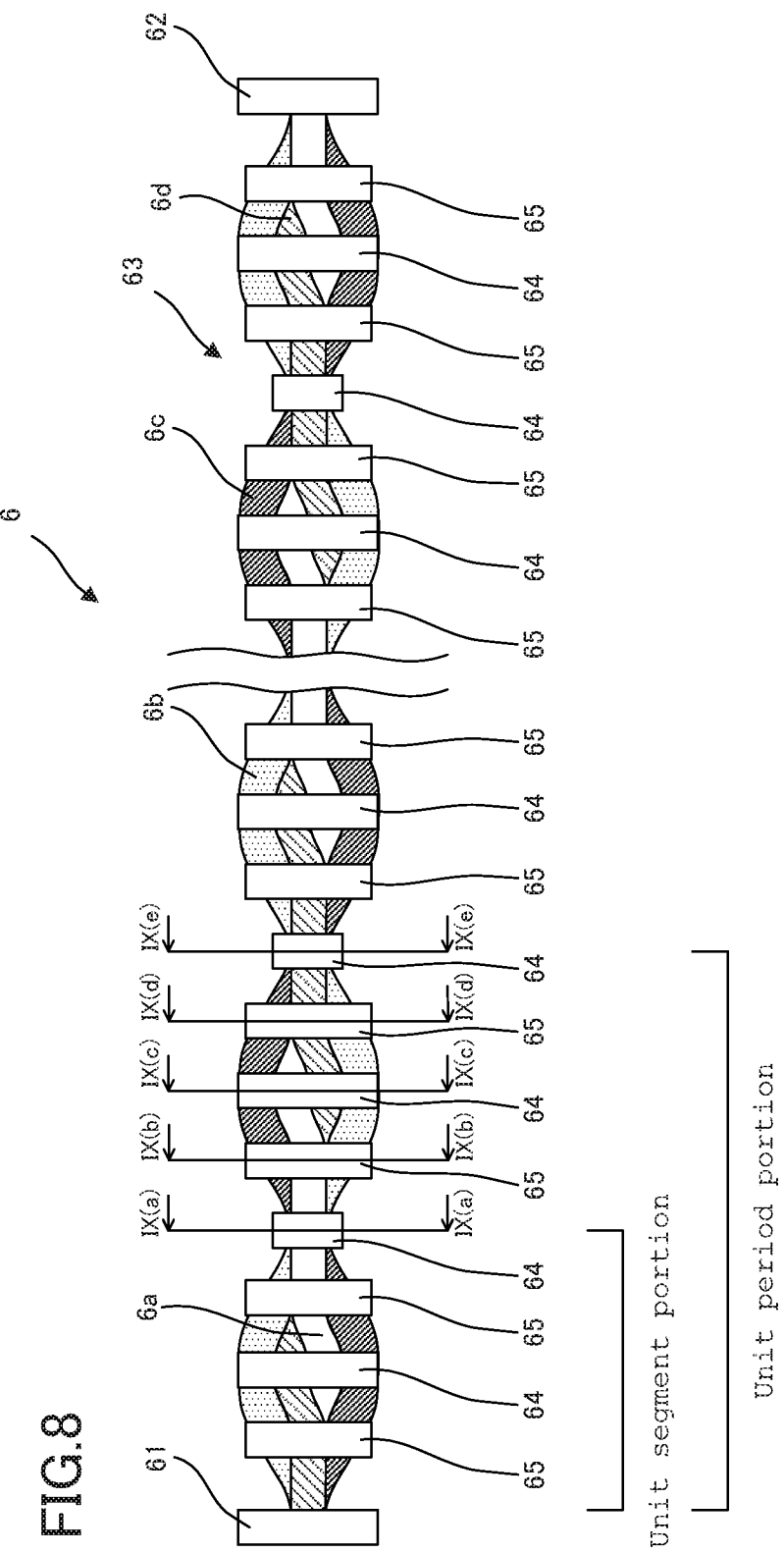

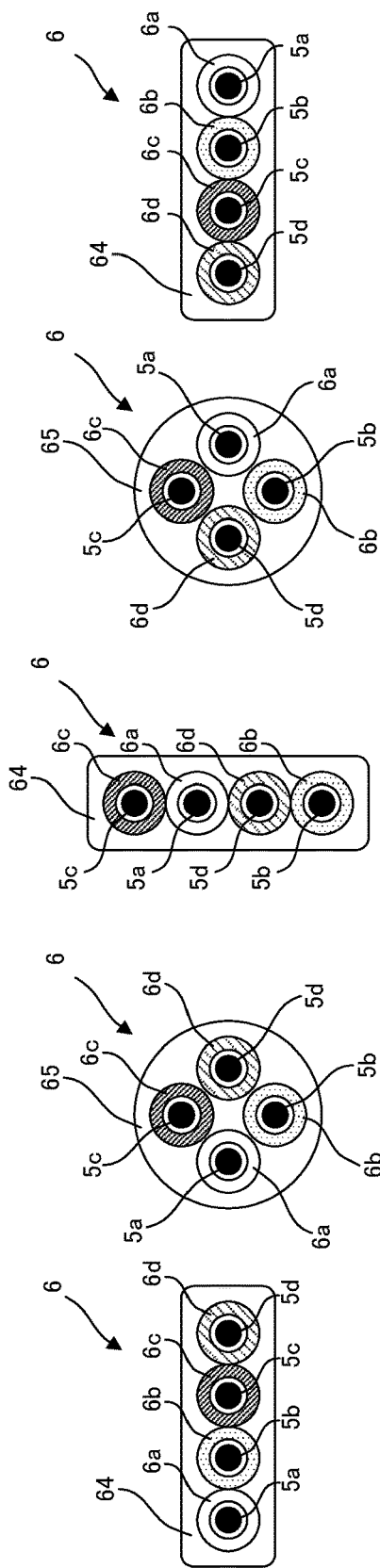

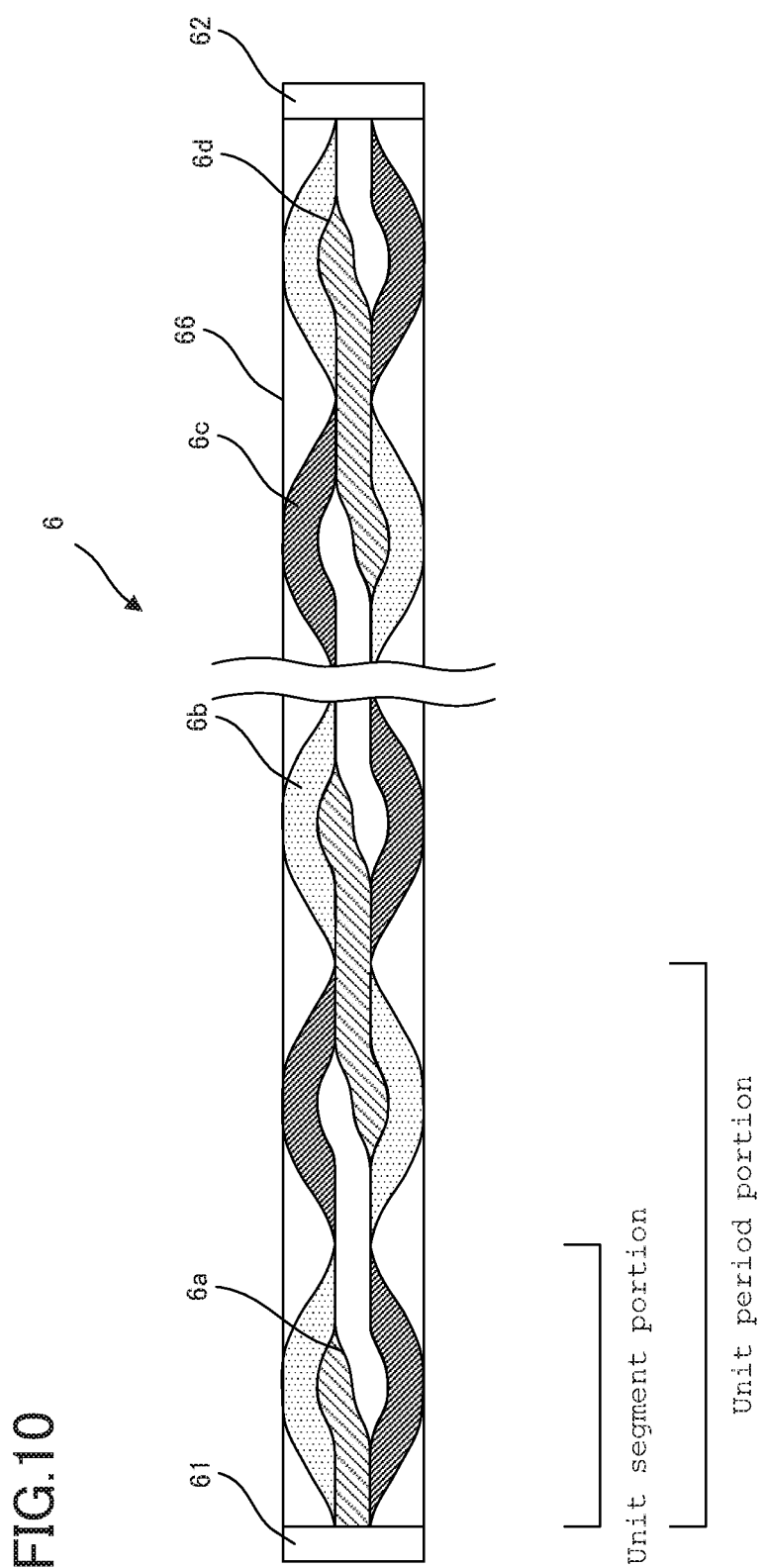

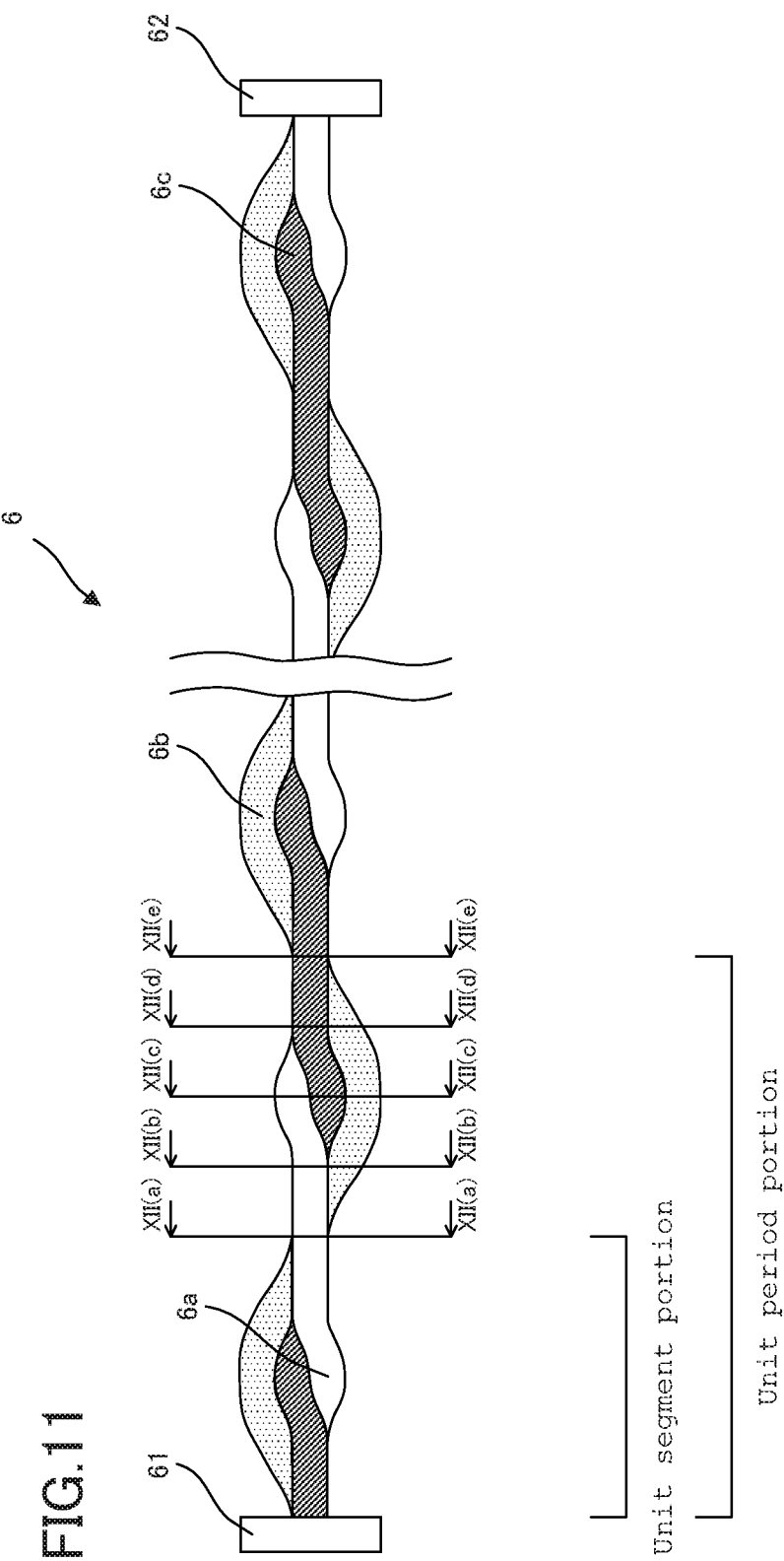

US 10,213,092 B2

SHEATH ASSEMBLY, MANIPULATOR, AND MANIPULATOR SYSTEM

CROSS-REFERENCE TO RELATED APPLICATIONS

This application is a continuation claiming priority on the basis of Japan Patent Application No. 2015-108235 applied in Japan on May 28, 2015 and based on PCT/JP2016/063348 filed on Apr. 28, 2016. The contents of both the PCT application and the Japan Application are incorporated herein by reference.

BACKGROUND OF THE INVENTION AND RELATED ART STATEMENT

The present invention relates to a sheath assembly through which linear members are movably inserted, a manipulator, and a manipulator system.

For instance, there has been a manipulator widely used in which treatment tools are inserted through the body cavity of a patient and a distal end of the treatment tool is pulled as by means of a wire for bending to view, and apply treatments to, organs in the body cavity. For surgical operations, a plurality of treatment tools such as an endoscope for viewing purposes, forceps adapted to take hold of tissues or an electric scalpel adapted to cut off tissues are often inserted through the body cavity.

Regarding such a prior art manipulator, U.S. Pat. No. 7,744,608 typically disclose a structure in which a plurality of sheaths for receiving a driving wire are twisted together thereby reducing a difference in the length of the path taken between the respective sheaths.

SUMMARY OF INVENTION

A sheath assembly according to one embodiment includes:

at least three tubular members through which linear members can be inserted, a first holder configured to hold one end side of the tubular members, and a second holder configured to hold the other end side of the tubular members, wherein:

the first holder and the second holder hold the at least three tubular members such that sections of the tubular members orthogonal to an axial direction thereof are linearly aligned, the at least three tubular members include a unit period portion having a given length such that the sections are repeatedly aligned in the same arrangement, in starting and terminating positions of the unit period portion, the sections are aligned linearly in the same first arrangement, and in an intermediate position between the starting and terminating positions of the unit period portion, the sections are aligned linearly in a second arrangement opposite to that in the staring and terminating positions.

BRIEF DESCRIPTION OF DRAWINGS

FIG. 3 is illustrative of a sheath assembly according to the first embodiment.

FIGS. 4A to 4H are a series of views of FIG. 3 as taken on sections IV(a) to IV(h) in directions indicated by arrows.

FIGS. 5A to 5E are illustrative of how to weave the sheath assembly according to the first embodiment.

FIG. 6 is illustrative of a sheath assembly according to the second embodiment.

FIG. 8 is illustrative of a sheath assembly according to the third embodiment.

FIGS. 9A to 9E are a series of views of FIG. 8 as taken on sections IX(a) to IX(e) in directions indicated by arrows.

FIG. 10 is illustrative of a sheath assembly according to the fourth embodiment.

FIG. 11 is illustrative of a sheath assembly according to the fifth embodiment.

DESCRIPTION OF EMBODIMENTS

Several embodiments will now be explained.

Figure 1:
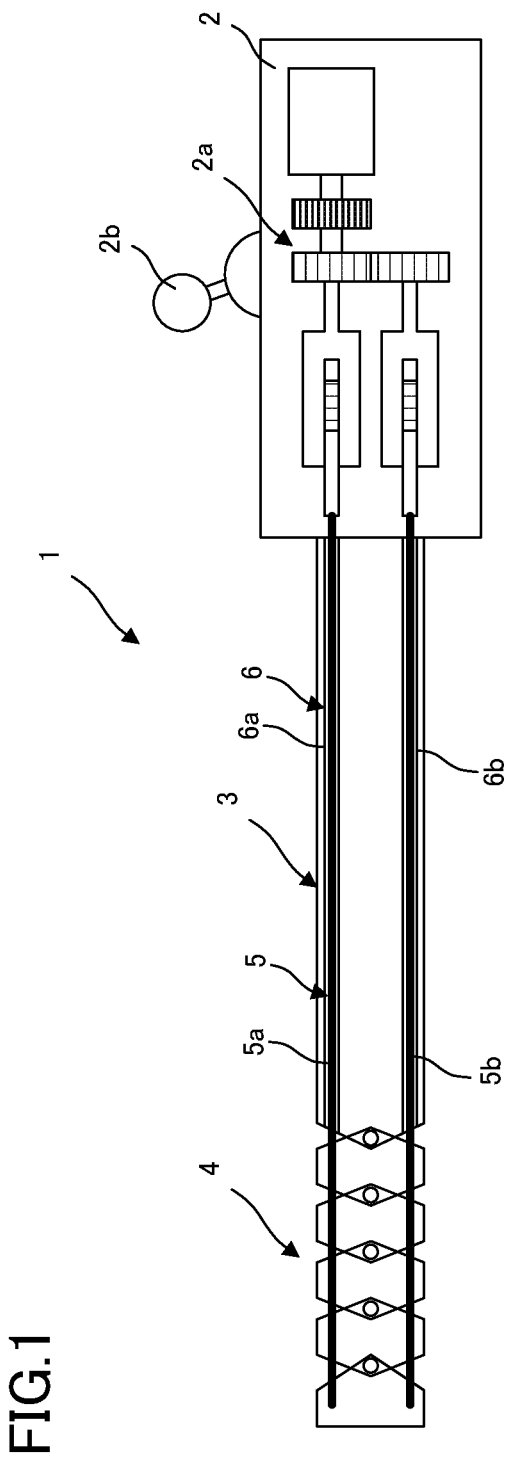
FIG. 1 is illustrative in schematic of the manipulator according to one embodiment.

FIG. 1 is illustrative in schematic of the manipulator 1 according to one embodiment.

The manipulator 1 described herein includes a main unit 2, an elongated portion 3 that extends from the main unit 2, a bending assembly 4 that is connected to the elongated portion 3, a linear member 5, such as a wire, for transmission of power that puts the bending assembly 4 into actuation, a sheath assembly 6 through which the linear member 5 is inserted.

The main unit 2 includes a driving unit 2a having a motor, gears and so on for generation of power to be transmitted to the linear member 5, and a drive operating unit 2b that actuates the driving unit 2a. The main unit 2 is in a casing form for accommodating the driving unit 2a. In the first embodiment, the elongated portion 3 adapted to accommodate the linear member 5 extends from the main unit 2. The elongated portion 3 is provided at its distal end with the bending assembly 4 that can be bent or curved relative to the elongated portion 3. The linear member 5 includes at least a first linear member 5a and a second linear member 5b, made up of a wire or the like, each of which is attached on one end side to the bending assembly 4 and passed through the elongated portion 3, and attached on the other end side to the driving unit 2a.

In the manipulator 1 having such structure, usually, the drive operating unit 2b is operated to bend the bending assembly 4. Operation of the drive operating unit 2b causes the driving unit 2a to be driven. By power generated by the driving unit 2a, the first linear member 5a in a first sheath 6a or the second linear member 5b in a second sheath 6b is pulled. The pulled linear member 5 moves through the elongated portion 3 accordingly to pull one side of the bending member 4 thereby bending the bending assembly 4. Although there are two power transmission members provided, it is to be understood that more power transmission members may be used. The more the power transmission members, the higher the degree of freedom in bending will become.

Figure 2:
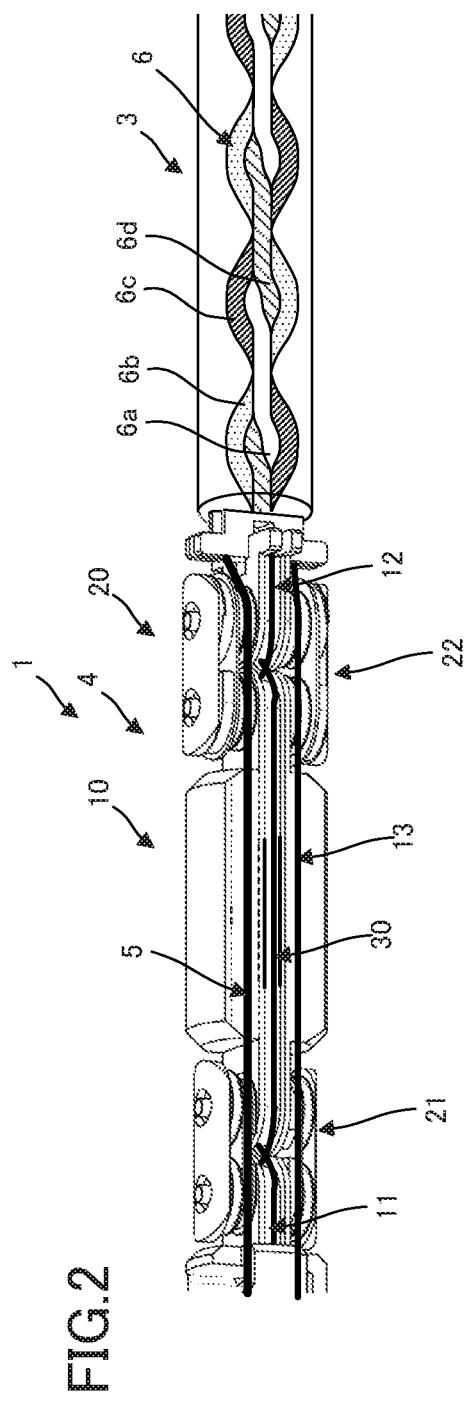
FIG. 2 is illustrative in part of the elongated (continuous) portion and bending assembly of the manipulator according to one embodiment.

FIG. 2 is illustrative in part of the elongated portion 3 and bending assembly 4 in the manipulator 1 according to the first embodiment.

The bending assembly 4 in the manipulator 1 described herein includes at least one joint portion 10. The joint portion 10 includes a first link member 11, a second link member 12, an intermediate link member 13 attached to between the first link member 11 and the second link member 12, a first coupling member 21 adapted to couple the first link member 11 to the intermediate link member 13, a second coupling member 22 adapted to couple the second link member 12 to the intermediate link member 13, and a defining member 30 that is formed typically of a linear member and wound about the first link member 11, the second link member 12 and the intermediate link member 13. Note here that the bending assembly 4 may be built up of a plurality of joint portions 10.

The elongated member 3 includes a sheath assembly 6 inside through which the linear member 5 is inserted. The sheath assembly 6 includes at least three tubular members woven together: a first sheath 6a, a second sheath 6b and a third sheath 6c that are received or accommodated in the elongated portion 3. As the driving unit 2a shown in FIG. 1 is driven, it causes the linear member 5 to move within the sheaths 6a, 6b and 6c to bend the bending assembly 4. The outer surfaces of the respective sheaths 6a, 6b and 6c have preferably a high degree of roughness so as to give large friction to portions where the sheaths 6a, 6b and 6c intersect.

FIG. 3 is illustrative of the sheath assembly 6 according to the first embodiment, and FIGS. 4A to 4H are views of FIG. 3 as taken on sections IV(a) to IV(h) in directions indicated by arrows.

The sheath assembly 6 according to the first embodiment described herein includes a first sheath 6a, a second sheath 6b, a third sheath 6c and a fourth sheath 6d each in the form of a tubular member. The first sheath 6a, the second sheath 6b, the third sheath 6c, and the fourth sheath 6d is held by a first holder 61 at one end and by a second holder 62 at the other end. The first holder 61, and the second holder 62 is formed as of a metal or resin, and has an opening through which the sheath 6 passes. The sheath assembly 6 is fixed in place by suitable means such as bonding, thermal fusion, soldering or brazing and so on.

As shown in FIGS. 4A to 4H, the first sheath 6a, the second sheath 6b, the third sheath 6c, and the fourth sheath 6d is provided through it with a first linear member 5a, a second linear member 5b, a third linear member 5c, and a fourth linear member 5d, respectively. Note here that there may be at least three sheath assemblies 6 provided.

The sheath assembly 6 has a structure in which the first sheath 6a, the second sheath 6b, the third sheath 6c and the fourth sheath 6d are woven together. As shown in FIG. 4A and as taken on section IV(a) in a direction indicated by arrows, there are the first sheath 6a, the second sheath 6b, the third sheath 6c and the fourth sheath 6d aligned linearly. Then, as shown in FIG. 4B and as taken on section IV(b) in a direction indicated by arrows, there are the third sheath 6c located above, the second sheath 6b located below, the first sheath 6a located on the left and the fourth sheath 6d located on the right: they are annularly aligned. Subsequently, as shown in FIG. 4C and as taken on section IV(c) in a direction indicated by arrows, the third sheath 6c, the first sheath 6a, the fourth sheath 6d and the second sheath 6b are aligned linearly from above. Then, as shown in FIG. 4D and as taken on section IV(d) in a direction indicated by arrows, there are the third sheath 6c located above, the second sheath 6b located below, the fourth sheath 6d located on the left and the first sheath 6a located on the right: they are annularly aligned.

Then, as shown in FIG. 4E and as taken on section IV(e) in a direction indicated by arrows, the fourth sheath 6d, the third sheath 6c, the second sheath 6b and the first sheath 6a are aligned linearly from the left. Then, as shown in FIG. 4F and as taken on section IV(f) in a direction indicated by arrows, there are the second sheath 6b located above, the third sheath 6c located below, the fourth sheath 6d located on the left and the first sheath 6a located on the right: they are annularly aligned. Then, as shown in FIG. 4G and as taken on section IV(g) in a direction indicated by arrows, the second sheath 6b, the fourth sheath 6d, the first sheath 6a and the third sheath 6c are aligned linearly from above. Then, as shown in FIG. 4H and taken on section IV(h) in a direction indicated by arrows, there are the second sheath 6b located above, the third sheath 6c located below, the first sheath 6a located on the left and the fourth sheath 6d located on the right: they are annularly aligned. And as taken on section IV(i) of FIG. 3 in a direction indicated by arrows, the first sheath 6a, the second sheath 6b, the third sheath 6c and the fourth sheath 6d are aligned linearly from the left, as is the case with section IV(a) in a direction indicated by arrows.

As taken on a certain section, the first sheath 6a, the second sheath 6b, the third sheath 6c and the fourth sheath 6d have alternately a site where they are linearly aligned and a site where they are annularly aligned at a predetermined interval. And, as taken on a certain section, the site where the first sheath 6a, the second sheath 6b, the third sheath 6c and the fourth sheath 6d are linearly aligned has alternately a site where they are aligned linearly in a given first direction and a site where they are aligned linearly in a second direction that is just or almost perpendicular to the first direction. In the example of FIG. 3, the first direction is defined by a direction perpendicular to a sheet plane and the second direction is defined by a vertical direction parallel with the sheet plane.

The first sheath 6a, the second sheath 6b, the third sheath 6c and the fourth sheath 6d are located such that axially orthogonal sections line up linearly for each unit segment portion, and they are aligned in the same direction and order for each unit period portion. That is, two unit segment portions define one unit period portion. Preferably, the sheath assembly 6 is formed by repetition of the unit period portion. While the length of the unit segment portion is preferably the same from site to site, it is to be understood that there may be a slight deviation acceptable.

In the example shown in FIG. 3, while the first holder 61 and the second holder 62 are located in positions where the sheaths 6a, 6b, 6c and 6d line up linearly in the first direction, it is to be noted that there are no limitation on them. For instance, the holders may be located in positions where the sheaths 6a, 6b, 6c and 6d line up linearly in the second direction or where they are annularly aligned.

FIGS. 5A to 5E are illustrative of how to weave the sheath assembly 6 according to the first embodiment.

First of all, the first sheath 6a, the second sheath 6b, the third sheath 6c and the fourth sheath 6d are put side by side as shown in FIG. 5A. Subsequently, as shown in FIG. 5A by an arrow A, a lower portion of the fourth sheath 6d is guided over the rears of the second sheath 6b and the third sheath 6c and then pulled out from between the first sheath 6a and the second sheath 6b to position it between the second sheath 6b and the third sheath 6c.

Then, as shown in FIG. 5B by an arrow B, a lower portion of the first sheath 6a is guided over the rears of the second sheath 6b and the fourth sheath 6d and then pulled out from between the third sheath 6c and the fourth sheath 6d to position it between the second sheath 6b and the fourth sheath 6d.

Then, as shown in FIG. 5C by an arrow C, a lower portion of the third sheath 6c is guided over the rears of the first sheath 6a and the fourth sheath 6d and then pulled out from between the first sheath 6a and the second sheath 6b to position it between the first sheath 6a and the fourth sheath 6d.

Then, as shown in FIG. 5D by an arrow D, a lower portion of the second sheath 6b is guided over the rears of the first sheath 6a and the third sheath 6c and then pulled out between the third sheath 6c and the fourth sheath 6d to position it between the first sheath 6a and the third sheath 6c.

Thereupon, as shown in FIG. 5E, the lower portions of the first sheath 6a, the second sheath 6b, the third sheath 6c and the fourth sheath 6d woven as shown in FIGS. 5A through 5D are placed in the same arrangement as in FIG. 5A. That is, if weaving is then continued in the same way as in FIGS. 5A through 5D, the first sheath 6a, the second sheath 6b, the third sheath 6c and the fourth sheath 6d will be woven together.

According to the sheath assembly 6 of the first embodiment wherein the first sheath 6a, the second sheath 6b, the third sheath 6c and the fourth sheath 6d are woven together, they are positioned such that for each section orthogonal to the lengthwise direction, they change positions in the vertical and lateral directions. It is thus possible to keep a plurality of sheaths stable without being raveled and reduce a difference in the length of the path taken between sheaths. It is also easy to fabricate the sheath assembly only by weaving.

Figure 7C:
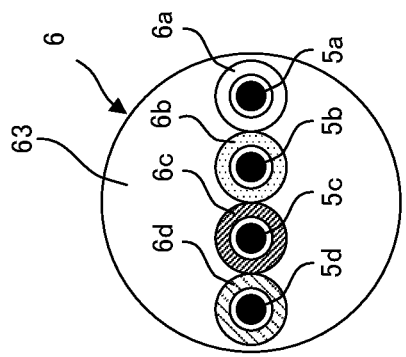
FIGS. 7A to 7c are a series of views of FIG. 6 as taken on sections VII(a) to VII(c) in directions indicated by arrows.
Figure 7B:
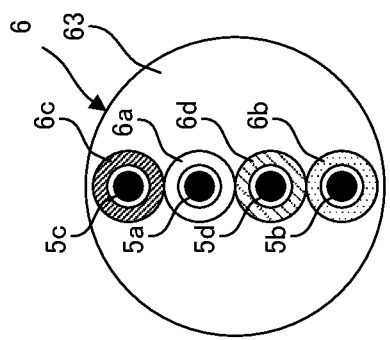
Figure 7A:
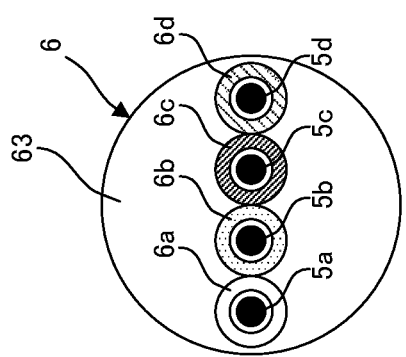

FIG. 6 is illustrative of the sheath assembly 6 according to the second embodiment, and FIGS. 7A to 7C are illustrative in section of the sheath assembly 6 at taken on sections VII(a) to VII(c) shown in FIG. 6 in a direction indicated by arrows.

The sheath assembly 6 according to the second embodiment includes an intermediate holder 63 adapted to hold woven sheaths 6a, 6b, 6c, and 6d in a linearly aligned state. Each of the intermediate holder 63 formed of a metal, resin or other similar material is round in sectional shape orthogonal to its lengthwise direction, and has an opening through which the sheath 6a, 6b, 6c, and 6d passes. The sheaths 6a, 6b, 6c and 6d are each fixed in place as by bonding, thermal fusion, soldering or brazing and so on. The first sheath 6a, the second sheath 6b, the third sheath 6c and the fourth sheath 6d are each held at its one end by a first holder 61 and at the other end by a second holder 62. The openings formed in the intermediate holders 63 in association with the first sheath 6a, the second sheath 6b, the third sheath 6c and the fourth sheath 6d may be coupled together or spaced away from one another. Note here that the number of openings formed in the intermediate holders 63 is preferably corresponding to the number of sheaths. In the second embodiment described herein, the openings provided in association with the first sheath 6a, the second sheath 6b, the third sheath 6c and the fourth sheath 6d may be coupled together or spaced away from one another.

As shown in FIGS. 7A to 7C, a first linear member 5a, a second linear member 5b, a third linear member 5c and a fourth linear member 5d are inserted through the first sheath 6a, the second sheath 6b, the third sheath 6c and the fourth sheath 6d, respectively.

The sheath assembly 6 has a structure in which the first sheath 6a, the second sheath 6b, the third sheath 6c and the fourth sheath 6d are woven together. As shown in FIG. 7A and as taken on section VII(a) that is the intermediate holder 63 in a direction indicated by arrows, the first sheath 6a, the second sheath 6b, the third sheath 6c and the fourth sheath 6d are aligned linearly from the left. Then, as shown in FIG. 7B and as taken on section VII(b) that is the intermediate holder 63 in a direction indicated by arrows, the third sheath 6c, the first sheath 6a, the fourth sheath 6d and the second sheath 6b are aligned linearly from above. Then, as shown in FIG. 7C and as taken on section VII(c) that is the intermediate holder 63 in a direction indicated by arrows, the fourth sheath 6d, the third sheath 6c, the second sheath 6b and the first sheath 6a are aligned linearly from the left.

By provision of the intermediate holder 63, it is thus possible to strengthen the force of holding the sheath assembly 6 thereby keeping a plurality of sheaths more stably without being raven. Note here that the intermediate holder 63 may have a structure in which the woven sheaths 6 are annularly arranged, and that the sectional shape orthogonal to the lengthwise direction of the intermediate holder 63 may be rectangular rather than round.

FIG. 8 is illustrative of the sheath assembly 6 according to the third embodiment, and FIGS. 9A to 9E are a series of views as taken on sections IX(a) to IX(e) shown in FIG. 8 in directions indicated by arrows.

The sheath assembly 6 according to the third embodiment includes a linear holder 64 adapted to hold the woven sheaths 6a, 6b, 6c and 6d in a linearly aligned state and an annular holder 65 adapted to hold the woven sheaths 6a, 6b, 6c and 6d in an annularly arranged state. The sectional shape of the linear holder 64 orthogonal to its lengthwise direction is rectangular, and has openings through which the sheaths 6a, 6b, 6c and 6d pass. The sectional shape of the annular holder 65 is round, and has openings through which the sheaths 6a, 6b, 6c and 6d pass. There are the sheaths 6a, 6b, 6c and 6d fixed as by bonding, thermal fusion, soldering or brazing and so on to the linear holder 64 and the annular holder 65 formed of a metal, resin or other similar material. Note here that the number of openings formed in the linear holder 64 and the annular holder 65 are preferably corresponding to the number of sheaths. In the third embodiment, the openings are provided in association with the first sheath 6a, the second sheath 6b, the third sheath 6c and the fourth sheath 6d, and may be coupled together or spaced away from one another.

The first sheath 6a, the second sheath 6b, the third sheath 6c and the fourth sheath 6d are each held at its one end by the first holder 61 and at the other end by the second holder 62. As shown in FIG. 9A to 9E, a first linear member 5a, a second linear member 5b, a third linear member 5c and a fourth linear member 5d are inserted through the first sheath 6a, the second sheath 6b, the third sheath 6c and the fourth sheath 6d, respectively.

The sheath assembly 6 has a structure in which the first sheath 6a, the second sheath 6b, the third sheath 6c and the fourth sheath 6d are woven together. As shown in FIG. 9A and as taken on section IX(a) in a direction indicated by arrows, the first sheath 6a, the second sheath 6b, the third sheath 6c and the fourth sheath 6d are aligned linearly from the left. Then, as shown in FIG. 9B and as taken on section IX(b) in a direction indicated by arrows, there are the third sheath 6c located above, the second sheath 6b located below, the first 6a located on the left and the fourth sheath 6d located on the right: they are annularly aligned. Subsequently, as shown in FIG. 9C and as taken on section IX(c) in a direction indicated by arrows, the third sheath 6c, the first sheath 6a, the fourth sheath 6d and the second sheath 6b are aligned linearly from above. Then, as shown in FIG. 9D and as taken on section IX(d) in a direction indicated by arrows, there are the third sheath 6c located above, the second sheath 6b located below, the fourth sheath 6d located on the left and the first sheath 6a located on the right: they are annularly aligned. Then, as shown in FIG. 9E and as taken on section IX(e) in a direction indicated by arrows, the fourth sheath 6d, the third sheath 6c, the second sheath 6b and the first sheath 6a are aligned linearly from the left. This way the unit segment comes to completion, and the unit period portion is woven in much the same sequence as in FIG. 4, followed by keeping on with weaving in a similar arrangement or sequence.

By provision of the linear holder 64 and the annular holder 65, it is thus possible to strengthen the force of holding the sheath assembly 6 and keep a plurality of sheaths more stably without being raven. Note here that the linear holder 64 and the annular holder 65 may also be configured in other shapes than the round or rectangular shape.

FIG. 10 is illustrative of the sheath assembly 6 according to the fourth embodiment.

According to the fourth embodiment, the sheath assembly 6 is received or accommodated in a cylindrical outer sheath while the sheaths are woven together. Note here that the woven sheath assembly 6 may have the same structure as is the case with the sheath assembly 6 according to the first embodiment shown in FIG. 3.

By receiving or accommodating the sheath assembly 6 within the covering member 66, it is thus possible to strengthen the force of holding the sheath assembly 6 and keep a plurality of sheaths more stably without being raven. Note here that the sectional shape of the covering member 66 orthogonal to its lengthwise direction may also have other configuration than the round or rectangular one.

FIG. 11 is illustrative of the sheath assembly 6 according to the fifth embodiment, and FIGS. 12A to 12E are a series of views as taken on sections XII(a) to XII(e) shown in FIG. 11 in directions indicated by arrows.

The sheath assembly 6 according to the fifth embodiment includes a first sheath 6a, a second sheath 6b, and a third sheath 6c. The first sheath 6a, the second sheath 6b and the third sheath 6c are each held at its one end by a first holder 61 and at the other end by a second holder 62. The first holder 61, and the second holder 62 is formed of a metal, resin or the like, and has an opening through which the sheath 6a, 6b, and 6c passes, and to which the sheath 6a, 6b, and 6c is fixed as by bonding, thermal fusion, soldering or brazing and so on.

As shown in FIGS. 12A to 12E, a first linear member 5a, a second linear member 5b and a third linear member 5c is inserted through the first sheath 6a, the second sheath 6b, and the third sheath 6c, respectively. Note here that the number of sheaths may be at least three.

Figure 12E:
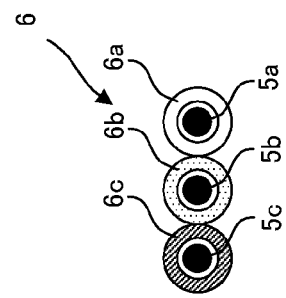
FIGS. 12A to 12E are a series of views of FIG. 11 as taken on sections XII(a) to XII(e) in directions indicated by arrows.
Figure 12D:
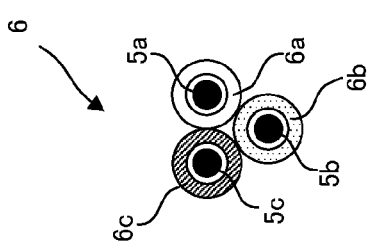
Figure 12C:
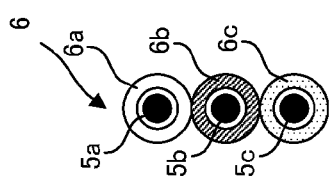
Figure 12B:
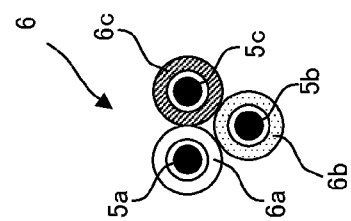
Figure 12A:
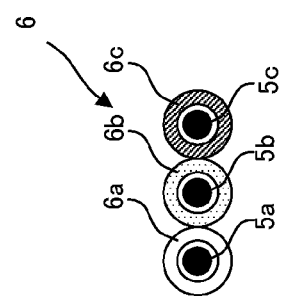

The sheath assembly 6 has a structure in which the first sheath 6a, the second sheath 6b and the third sheath 6c are woven together. As shown in FIG. 12A and as taken on section XII(a) in a direction indicated by arrows, the first sheath 6a, the second sheath 6b and the third sheath 6c are aligned linearly from the left. Then, as shown in FIG. 12B and taken on section XII(b) in a direction indicated by arrows, there are the first sheath 6a and the third sheath 6c located above and the second sheath 6b located below: they are annularly aligned. Subsequently, as shown in FIG. 12C and as taken on section XII(c) in a direction indicated by arrows, the first sheath 6a, the second sheath 6b and the third sheath 6c are aligned linearly from above. Then, as shown in FIG. 12D and as taken on section XII(d) in a direction indicated by arrows, there are the first sheath 6a located above, the second sheath 6b located halfway on the left and the third sheath 6c located below: they are annularly aligned. Then, as shown in FIG. 12E and as taken on section XII(e) in a direction indicated by arrows, the third sheath 6c, the second sheath 6b and the first sheath 6a are aligned linearly from the left. The unit segment portion is completed in this way, and the unit period portion is then woven, followed by keeping on with weaving in a similar alignment or sequence.

Thus, as taken on a certain section, a site where the first sheath 6a, the second sheath 6b and the third sheath 6c are linearly aligned alternates with a site where they are annularly aligned at a given interval, and again as taken on a certain section, a site where the first sheath 6a, the second sheath 6b and the third sheath 6c are linearly aligned in a given first direction alternates with a site where they are linearly aligned in a second direction just or almost perpendicular to the first direction. In the example shown in FIG. 12A to 12E, the first direction is defined by a direction perpendicular to the sheet plane whereas the second direction is defined by a vertical direction parallel with the sheet plane.

The first sheath 6a, the second sheath 6b and the third sheath 6c are aligned linearly in the same direction for each unit segment, and in the same direction and order for each unit period portion. In other words, two unit segments define one unit period. Preferably, the sheaths 6a, 6b and 6c are formed by repetition of the unit segment. While the unit segment has preferably the same length from site to site, it is to be understood that there is a slight deviation acceptable.

In the example shown in FIG. 12A to 12E, the first holder 61 and the second holder 62 are located in such positions as to allow the first sheath 6a, the second sheath 6b and the third sheath 6c to be aligned linearly in the first direction, but they may otherwise be located in any desired positions. For instance, they may be located in positions where the sheaths 6 are aligned linearly in the second direction or done annularly.

As is the case with the sheath assembly 6 according to the fifth embodiment, at least three sheaths: the first sheath 6a, the second sheath 6b and the third sheath 6c are woven together such that for each section orthogonal to the lengthwise direction, they vary in position alternately in the vertical direction and in the lateral direction. It is thus possible to hold a plurality of sheaths stably without being raven and reduce a difference in the length of the path taken between the sheaths. Weaving is all that is needed for easy fabrication of the sheath assembly.

Figure 13:
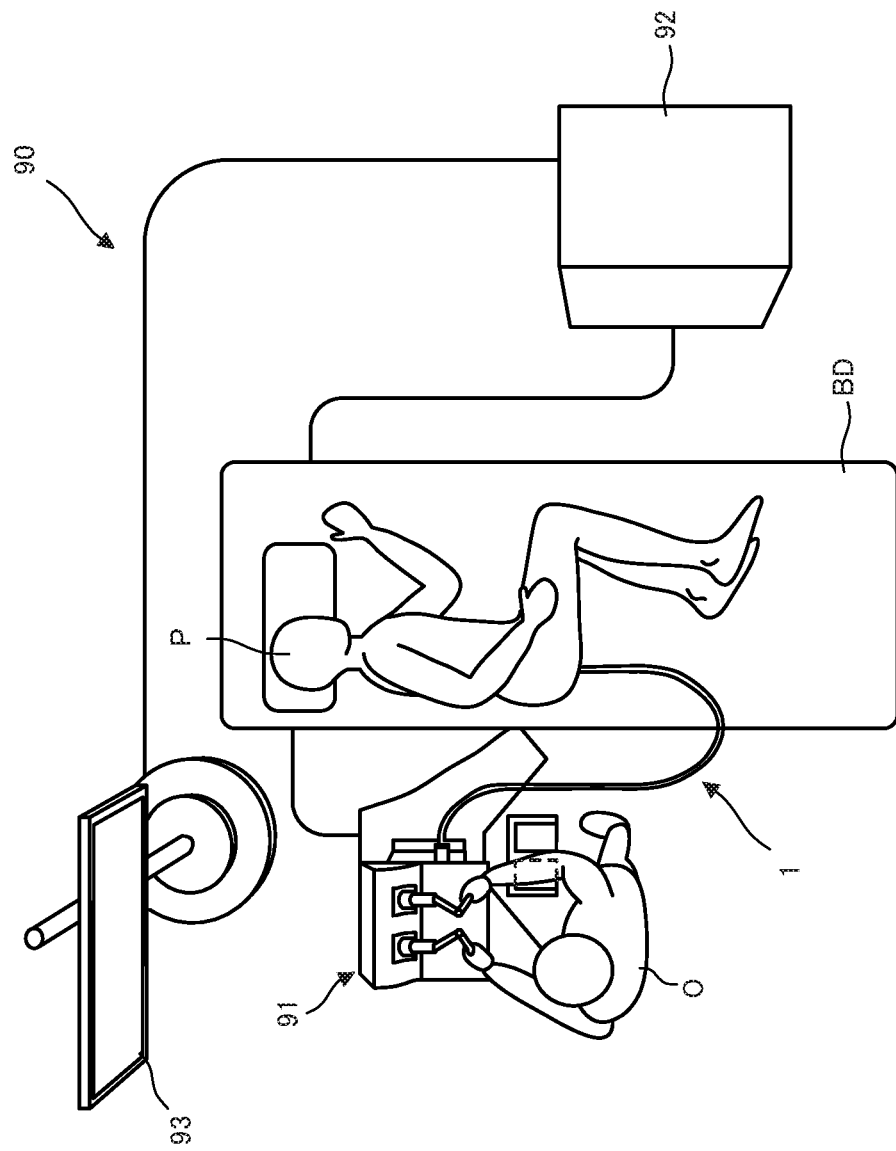
FIG. 13 shows a manipulator system to which the manipulator described herein is applied.
Figure 14:
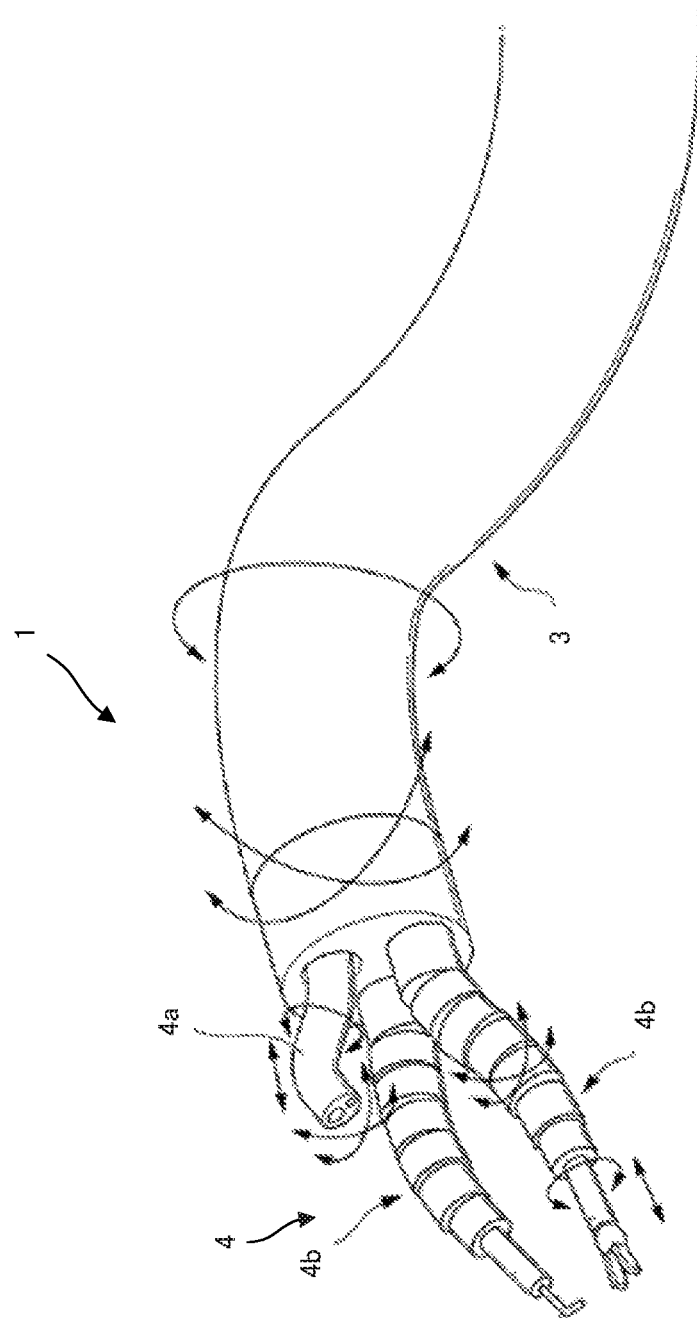
FIG. 14 is illustrative of one example of the bending assembly in the manipulator described herein.
Figure 15:
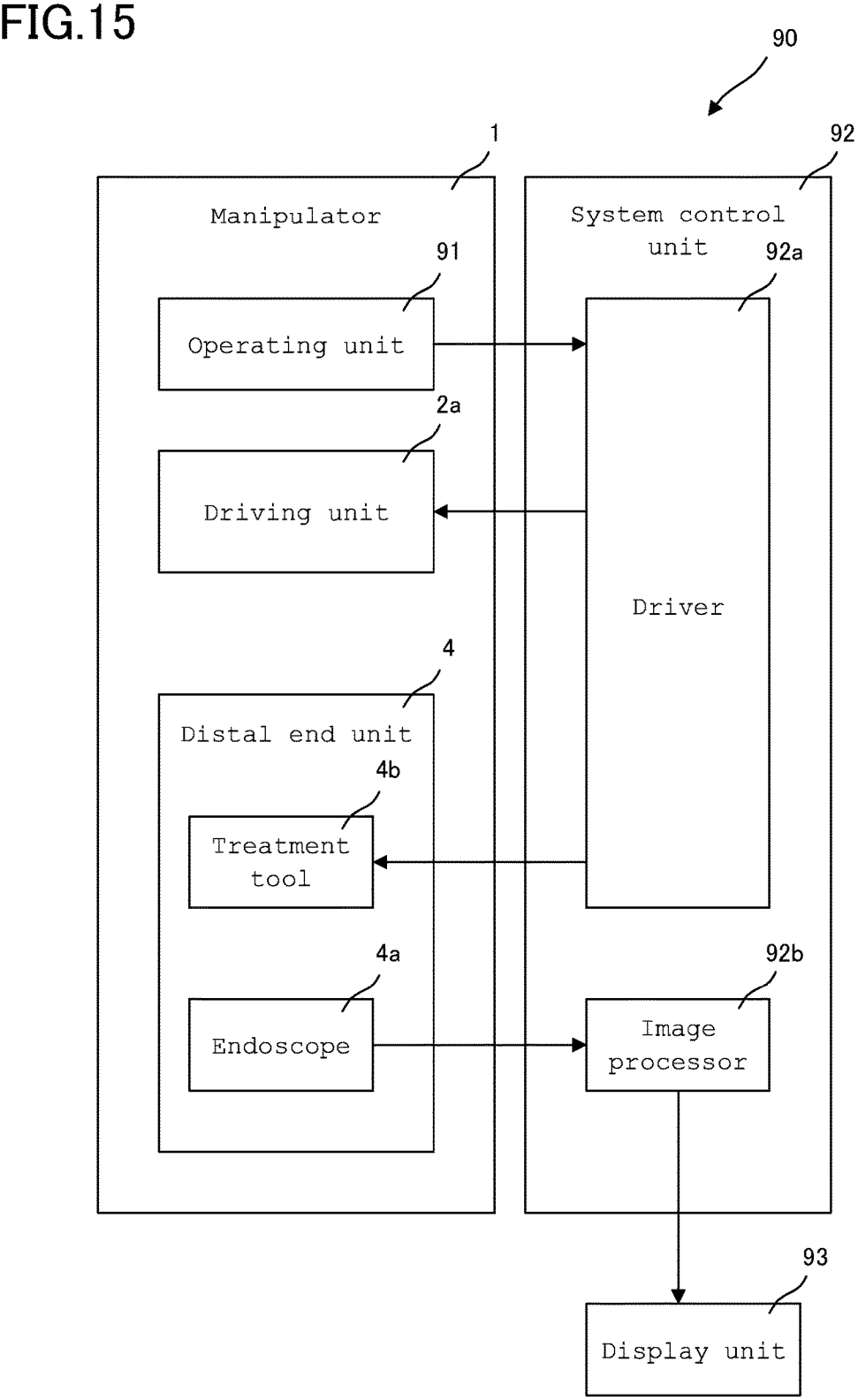
FIG. 15 is illustrative in architecture of the manipulator system to which the manipulator described herein is applied.

FIG. 13 is illustrative of the manipulator system 90 to which the manipulator 1 described herein is applied. FIG. 14 is illustrative of one example of the bending assembly 4 in the manipulator 1 described herein, and FIG. 15 is illustrative in architecture of the manipulator system 90 incorporating the manipulator 1 described herein.

The manipulator 1 shown in FIG. 1 is applied to a manipulator system 90 according to the embodiment described just below. The manipulator 90 includes a manipulator 1 including an operating unit 91 that is put by an operator O into operation, an elongated member 3 of FIG. 1 that can be inserted through the body cavity of a patient P lying down on an operating table BD, for instance, a soft internal organ such as the large intestine, and a bending assembly 4 of FIG. 1 that includes an endoscope attached to the distal end of the elongated member 3 and so on, a control unit 92 for controlling the manipulator 1, and a display unit 93 configured to display images acquired by way of the manipulator 1.

As shown in FIG. 13, the operating unit 91 includes a pair of operating handles attached to an operating table, a foot-switch located on a floor surface and so on. The operating unit 91 may have a multi-joint structure. The operating unit 91 is mechanically connected to the elongated member 3 and bending assembly 4 for bending of the elongated member 3. The control unit 92 uses an angle acquirement means such as an encoder to acquire the angle of the operating unit 91 in operation thereby actuating the bending assembly 4 by way of a driver 92a in response to the acquired signals.

As shown in FIG. 14, the manipulator 1 may include as the bending assembly 4 an endoscope 4a and a curving or bending treatment tool 4b. Alternatively, the bending assembly 4 may be a bending guide tube through which a conventional joint-free treatment tool is passed. The endoscope 4a is equipped with a viewing and illuminating optical system adapted to illuminate the body cavity to acquire images, an imaging device, and so on. The images obtained by the imaging device through the viewing optical system are produced out to an image processor 92b in the control unit 92, and the images processed in the image processor 92b are displayed on the display unit 93. Then, the operator O operates the manipulator 1 while viewing the images displayed on the display unit 93.

According to such manipulator system 90, stable and smooth operations can be achieved.

The sheath assembly 6 according to one embodiment described above includes at least three flexible sheaths 6a, 6b and 6c through which linear members can be inserted, a first holder 61 configured to hold one end side of the sheaths 6a, 6b and 6c, and a second holder 62 configured to hold the other end side of the sheaths 6a, 6b and 6c, wherein the first holder 61 and the second holder 62 hold the at least three sheaths 6a, 6b and 6c such that the sections of the sheaths 6a, 6b and 6c orthogonal to an axial direction thereof are linearly aligned. It is thus possible to hold three or more sheaths 6a, 6b and 6c unerringly in place and reduce a difference in the length of the path between the sheaths 6a, 6b and 6c.

In the sheath assembly 6 according to one embodiment, the at least three sheaths 6a, 6b and 6c include a unit period portion having a given length such that the sections are repeatedly aligned in the same arrangement; in starting and terminating positions of the unit period portion, the sections are aligned linearly in the same first arrangement; and in an intermediate position between the starting and terminating positions of the unit period portion, the sections are aligned linearly in a second arrangement opposite to that in the staring and terminating positions. It is thus possible to strengthen the force of holding the sheaths 6a, 6b and 6c together in place.

In the sheath assembly 6 according to one embodiment, the first holder 61 and the second holder 62 hold both ends of the sheaths 6a, 6b and 6c having the sections aligned linearly in the first arrangement. It is thus easy to insert the linear members through the sheath assembly 6.

In the sheath assembly 6 according to one embodiment, one of the first holder 61 and the second holder 62 holds one ends of the sheaths 6a, 6b and 6c having the sections aligned linearly in the first arrangement, and the other holds the other ends of the sheaths 6a, 6b and 6c having the sections aligned linearly in the second arrangement. Length can thus be determined on the basis of the unit segment portion shorter than the unit period portion so that there can be an increase in the degree of freedom in the length of the sheaths 6a, 6b and 6c.

The sheath assembly 6 according to one embodiment further includes an intermediate holder 63 configured to hold the sheaths 6a, 6b and 6c between the starting position of the unit period portion and the intermediate position and between the terminating position and the intermediate position. It is thus possible to strengthen the force of holding the sheaths 6a, 6b and 6c together in place.

In the sheath assembly 6 according to one embodiment, the intermediate holder 63 includes a rectangular, linear holder portion 64 configured to hold the sections of the sheaths 6a, 6b and 6c in such a way as to align them linearly, and a circular, annular holder portion 65 configured to hold the sections of the sheaths 6a, 6b and 6c in such a way as to align them annularly. It is thus possible to strengthen the force of holding the sheaths 6a, 6b and 6c together in place.

In the sheath assembly 6 according to one embodiment, the sheaths 6a, 6b and 6c are woven together so that the force of holding the sheaths 6a, 6b and 6c together in place can be strengthened.

The sheath assembly 6 according to one embodiment further includes a covering member 66 adapted to cover up an outer circumference of the sheaths 6a, 6b and 6c. It is thus possible to strengthen the force of holding the sheaths 6a, 6b and 6c together in place.

According to one embodiment, a manipulator 1 includes a driving unit 2a, a bending assembly 4 that is bent as the driving unit 2a is driven, at least three linear members 5a, 5b and 5c for transmission of driving force of the driving unit 2a to the bending assembly 4, and a sheath assembly 6 including sheaths 6a, 6b and 6c through which the linear members 5a, 5b and 5c are inserted. It is thus possible to hold three or more sheaths 6a, 6b and 6c unerringly in place and reduce a difference in the length of the path between the sheaths 6a, 6b and 6c thereby making sure smooth operations.

According to one embodiment, a manipulator system 90 includes a manipulator 1 including a treatment tool 4b and an endoscope 4a at a bending assembly 4, an image processor 92a adapted to apply image processing to an image signal obtained from the endoscope 4a, and a display unit 93 configured to display an image signal transmitted from the image processor 92a. Thus, the sheath assembly 6 used with the manipulator 1 allows three or more sheaths 6a, 6b and 6c to be unerringly held, and it is possible to reduce a difference in the length of the path between the sheaths 6a, 6b and 6c thereby ensuring smooth operation of the manipulator system 90.

It is here to be appreciated that the invention is in no sense limited to such embodiments as described above. While the explanation of some embodiments embraces numerous specific details for illustration, it would be obvious to those skilled in the art that diverse variations or modifications made thereto are included within the scope of the invention. In other words, illustrative embodiments of the invention are described without excluding generality from the claimed inventions and imposing any limitation thereon.

REFERENCE SIGNS LIST

1: Manipulator
2: Main unit
3: Elongated portion
4: Bending assembly

5: Linear member
6: Sheath assembly
6a: First sheath (tubular member)
6b: Second sheath (tubular member)
6c: Third sheath (tubular member)
6d: Fourth sheath (tubular member)
61: First holder
62: Second holder
63: Intermediate holder
64: Linear holder portion
65: Annular holder portion
66: Covering member
90: Manipulator system
91: Operating unit
92: System control unit
93: Display unit

The invention claimed is:

1. A sheath assembly comprising:
at least three tubular members through which linear members can be inserted;
a first holder configured to hold one end side of the tubular members;
a second holder configured to hold the other end side of the tubular members; and
an intermediate holder configured to hold the tubular members between a starting position of a unit period portion and an intermediate position and between a terminating position and the intermediate position;
wherein:
the first holder and the second holder hold the at least three tubular members such that sections of the tubular members orthogonal to an axial direction thereof are linearly aligned,
the at least three tubular members include a unit period portion having a given length such that the sections are repeatedly aligned in the same arrangement,
the intermediate holder includes a rectangular linear holder portion for holding the sections of the tubular members in such a way as to align them linearly, and a circular, annular holder portion for holding the sections of the tubular members in such a way as to align them annularly,
in the starting and terminating positions of the unit period portion, the sections are aligned linearly in the same first arrangement, and
in the intermediate position between the starting and terminating positions of the unit period portion, the sections are aligned linearly in a second arrangement opposite to that in the starting and terminating positions.

2. The sheath assembly according to claim 1, wherein the first holder and the second holder hold both ends of the tubular members having the sections aligned linearly in the first arrangement.

3. The sheath assembly according to claim 1, wherein one of the first holder and the second holder holds one ends of the tubular members having the sections aligned linearly in the first arrangement, and the other of the first holder and the second holder holds the other ends of the tubular members having the sections aligned linearly in the second arrangement.

4. The sheath assembly according to claim 1, wherein the tubular members are woven.

5. The sheath assembly according to claim 1, further comprising a covering member adapted to cover an outer circumference of the tubular members.

6. A manipulator comprising:
a bending assembly;
a driving unit configured to generate a driving force;
at least three linear members configured to transmit the driving force to the bending assembly;
at least three tubular members through which the linear members can be inserted;
a first holder configured to hold one end side of the tubular members; and
a second holder configured to hold an other end side of the tubular members;
wherein:
the first holder and the second holder hold the at least three tubular members such that sections of the tubular members orthogonal to an axial direction thereof are linearly aligned;
the at least three tubular members include a unit period portion having a given length such that the sections are repeatedly aligned in the same arrangement;
in starting and terminating positions of the unit period portion, the sections are aligned linearly in the same first arrangement;
in an intermediate position between the starting and terminating positions of the unit period portion, the sections are aligned linearly in a second arrangement opposite to that in the starting and terminating positions; and
each of the linear members is inserted in each of the tubular members.

7. A manipulator system comprising:
a manipulator according to claim 6;
an endoscope;
an image processor adapted to apply image processing to an image signal obtained from the endoscope; and
a display unit configured to display an image signal transmitted from the image processor.

8. The manipulator according to claim 6, wherein the first holder and the second holder hold both ends of the tubular members having the sections aligned linearly in the first arrangement.

9. The manipulator according to claim 6, wherein one of the first holder and the second holder holds one ends of the tubular members having the sections aligned linearly in the first arrangement, and the other of the first and second holders holds the other ends of the tubular members having the sections aligned linearly in the second arrangement.

10. The manipulator according to claim 6, further comprising an intermediate holder configured to hold the tubular members between the starting position of the unit period portion and the intermediate position and between the terminating position and the intermediate position.

11. The manipulator according to claim 10, wherein the intermediate holder includes a rectangular, linear holder portion for holding the sections of the tubular members in such a way as to align them linearly and a circular annular holder portion for holding the sections of the tubular members in such a way as to align them annularly.

12. The manipulator according to claim 6, wherein the tubular members are woven.

13. The manipulator according to claim 6, further comprising a covering member adapted to cover up an outer circumference of the tubular member.

* * * * *